US00PP29006P2

(12) United States Plant Patent
Farrow

(10) Patent No.: US PP29,006 P2
(45) Date of Patent: Feb. 27, 2018

(54) ***LAGERSTROEMIA* PLANT NAMED 'CONLAGRAS'**

(50) Latin Name: *Lagerstroemia indica*
Varietal Denomination: Conlagras

(71) Applicant: The Conard-Pyle Company, West Grove, PA (US)

(72) Inventor: Michael W. Farrow, Warwick, MD (US)

(73) Assignee: The Conard-Pyle Company, West Grove, PA (US)

( * ) Notice: Subject to any disclaimer, the term of this patent is extended or adjusted under 35 U.S.C. 154(b) by 0 days.

(21) Appl. No.: 15/530,153

(22) Filed: Dec. 7, 2016

(51) Int. Cl.
*A01H 5/00* (2006.01)

(52) U.S. Cl.
USPC ..... Plt./252

(58) Field of Classification Search
USPC ..... Plt./226, 252
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Lagerstroemia* plant named 'Conlagras', characterized by its rose-colored flowers, medium green colored foliage, and moderately vigorous, compact, low-mounded growth habit, is disclosed.

1 Drawing Sheet

Latin name of genus and species of plant claimed: *Lagerstroemia indica.*

Variety denomination: 'Conlagras'.

BACKGROUND OF THE INVENTION

The present invention relates to a new and distinct cultivar of *Lagerstroemia* plant botanically known as *Lagerstroemia indica* and hereinafter referred to by the cultivar name 'Conlagras'.

The new cultivar originated in a controlled breeding program in Earleville, Md. during spring 2009. The objective of the breeding program was the development of *Lagerstroemia* cultivars having abundant inflorescences with attractive flower coloration and compact growth habit.

The new *Lagerstroemia* cultivar is the result of open-pollination. The female (seed) parent of the new cultivar is 'Centennial', not patented, characterized by its dark purple-colored flowers, medium green-colored foliage, and compact, globular growth habit. The male (pollen) parent of the new cultivar is unknown. The new cultivar was discovered and selected as a single flowering plant within the progeny of the above stated open-pollination during July 2009 in a controlled environment in Earleville, Md.

Asexual reproduction of the new cultivar by terminal stem cuttings since August 2009 in West Grove, Pa. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Conlagras' as a new and distinct cultivar of *Lagerstroemia* plant:

1. Rose-colored flowers;
2. Medium green-colored foliage; and
3. Moderately vigorous, compact, low-mounded growth habit.

Plants of the new cultivar differ from plants of the female parent primarily in flower color and in having a more compact-mounded growth habit.

Of the many commercially available *Lagerstroemia* cultivars, the most similar in comparison to the new cultivar is INFINITINI Magenta 'G2X133271', U.S. Plant Pat. No. 24,474. However, in side-by-side comparisons, plants of the new cultivar differ from plants of 'G2X133271' in at least the following characteristics:

1. Plants of the new cultivar are have more branches than plants of 'G2X133271'; and
2. Plants of the new cultivar are earlier to flower than plants of 'G2X133271'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Conlagras'. The plants are approximately five-months old and were grown outside in one-gallon nursery-trade containers for four months in West Grove, Pa.

DETAILED BOTANICAL DESCRIPTION

Figure 1:
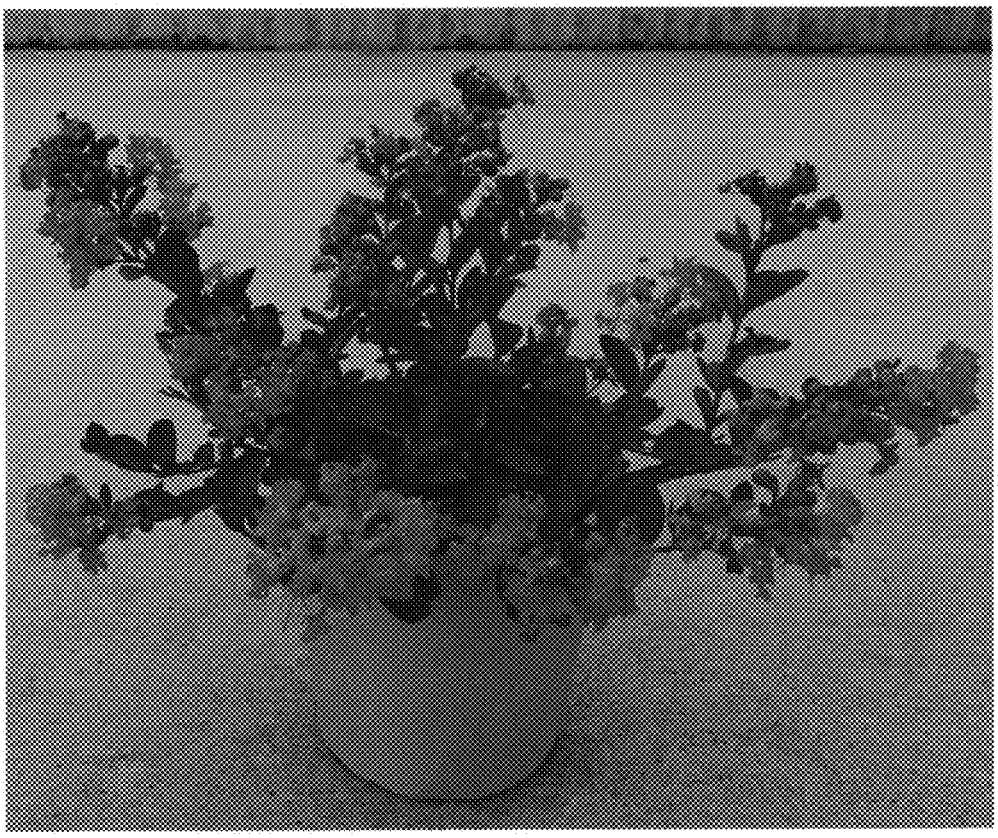
FIG. 1 illustrates a side view of the overall growth and flowering habit of 'Conlagras'.
Figure 2:
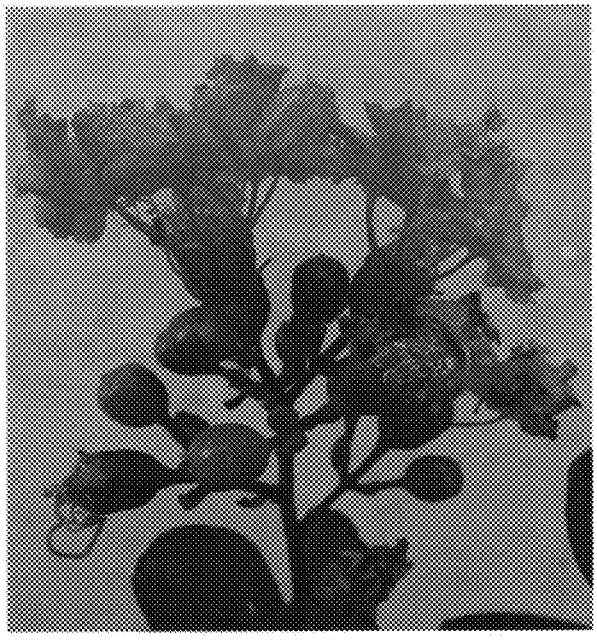
FIG. 2 illustrates a close-up view of an individual inflorescence of 'Conlagras'

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2016 under natural light conditions in West Grove, Pa.

The following descriptions and measurements describe approximately five-month old plants produced from cuttings from stock plants and grown under conditions comparable to those used in commercial practice. Plants were grown outside in one-gallon nursery-trade containers for four months in West Grove, Pa. Measurements and numerical values represent averages of typical plants.

Botanical classification: *Lagerstroemia indica* cultivar Conlagras.

Parentage:

*Female parent.*—*Lagerstroemia indica* 'Centennial', not patented.

*Male parent.*—Unknown.

Propagation:

*Type cutting.*—Terminal cuttings

*Time to initiate roots.*—Approximately 16 days.

*Time to produce a rooted cutting.*—Approximately 39 days.

*Root description.*—Fibrous and fine; white to brown in color.

*Rooting habit.*—Freely branching; dense.

Plant description:

*Commercial crop time.*—Approximately 15 weeks from a rooted cutting to finish in a 19.0 cm pot.

*Growth habit and general appearance.*—Multi-stemmed deciduous shrub, moderately vigorous, compact, low-mounded growth habit.

*Hardiness.*—USDA Zone 6b (−5° F.).

*Heat tolerance.*—Regularly tolerates temperatures as high as 39.4° C. (103° F.) in the summer.

*Size.*—Height from soil level to top of plant plane: Approximately 23.0 cm to 26.0 cm. Width: Approximately 30.0 cm to 34.0 cm.

*Branching habit.*—Freely branching. Pinching enhances branching. Quantity of lateral branches per plant: Approximately 5 main stems per plant with approximately 5 lateral branches per stem.

*Trunk.*—Diameter at soil level: Approximately 6.0 mm. Diameter at midpoint: Approximately 3.0 mm. Texture: Woody, slight exfoliation with age. Color: 200A.

*Branch.*—Shape: Quadrangulate with rounded wings. Strength: Strong. Arrangement: Subopposite to alternate. Aspect: Erect to 45° angle from main stem. Length to base of inflorescence: Approximately 17.0 cm to 22.0 cm. Diameter: Approximately 3.0 mm. Length of central internode: Approximately 3.0 cm. Texture of young stem: Glabrous. Texture of mature stem: Woody, rough. Color of young stem: 59B. Color of mature stem: 200A.

Foliage description:

*General description.*—Form: Simple. Arrangement: Subopposite to alternate. Fragrance: None detected.

*Leaves.*—Shape: Ovate to elliptic. Margin: Entire. Apex: Cuspidate. Base: Attenuate. Venation pattern: Pinnate. Length of mature leaf: Approximately 4.0 cm. Width of mature leaf: Approximately 2.5 cm. Texture of upper and lower surfaces: Glabrous. Color of upper surface of young foliage: 138A with venation color of 138D. Color of lower surface of young foliage: 138A with venation color of 138B. Color of upper surface of mature foliage: 137A with venation color of 137B. Color of lower surface of mature foliage: 138B with venation color of 138D.

*Petiole.*—Length: Approximately 1.0 mm. Diameter: Approximately 1.5 mm. Texture: Glabrous. Color: 176D.

Flowering description:

*Flowering season.*—Flowers in mid-summer through early fall.

*Lastingness of individual inflorescence on the plant.*—Approximately 1 to 2 weeks.

*General description.*—Type: Panicle, flowers self-cleaning. Quantity per plant: Approximately 20. Fragrance: Faint sweet. Aspect: Upward to outward. Height: Approximately 9.0 cm. Width: Approximately 7.0 cm. Quantity of flowers per inflorescence: Approximately 20.

*Peduncle.*—Strength: Strong. Shape: Rounded. Aspect: Erect to about 45° from branch axis. Length: Approximately 1.0 cm. Diameter: Approximately 2.0 mm. Texture: Glabrous. Color: 59C.

Flower description:

*Bud just before opening.*—Shape: Globose. Length: Approximately 6.0 mm. Diameter: Approximately 6.0 mm. Color: 59C.

*Corolla.*—Shape: Rotate. Depth: Approximately 1.0 cm. Diameter: Approximately 3.0 cm.

*Petals.*—Shape: Ovate. Margin: Crisped, undulating. Apex: Acute. Base: Truncate. Length: Approximately 1.6 cm. Width: Approximately 1.3 cm. Texture of upper and lower surfaces: Glabrous. Color of upper and lower surfaces: N57A.

*Calyx.*—Shape: Round. Depth: Approximately 6.0 mm. Diameter: Approximately 6.0 mm.

*Sepals.*—Shape: Triangular. Margin: Smooth, entire. Apex: Acute. Base: Truncate. Length: Approximately 3.0 mm. Width: Approximately 3.0 mm. Texture of upper surface: Glabrous. Texture of lower surface: Glabrous. Color of upper surface: 59C. Color of lower surface: 149D.

*Pedicel.*—Strength: Strong. Aspect: Erect, to about 45° from peduncle axis. Length: Approximately 6.0 mm. Diameter: Approximately 1.5 mm. Texture: Glabrous. Color: 59C.

*Reproductive organs.*—Androecium: Stamen quantity per flower: Approximately 30 to 36. Stamen length: Approximately 9.5 mm. Filament color: 62A. Anther shape: Narrow oblong, dorsifixed. Anther length: Approximately 8.0 mm. Anther color: 14B. Pollen amount: Abundant. Pollen color: 14B. Gynoecium: Pistil quantity per flower: 1. Pistil length: Approximately 1.6 cm. Stigma shape: Rounded. Stigma color: 133A. Style length: Approximately 1.3 cm. Style color: 59C. Ovary length: Approximately 3.0 mm. Ovary color: 3A.

Seed and fruit production: Neither seed nor fruit production has been observed.

Disease and pest resistance: Resistance to pathogens and pests common to *Lagerstroemia* has not been observed.

What is claimed is:

1. A new and distinct cultivar of *Lagerstroemia* plant named 'Conlagras', substantially as herein illustrated and described.

* * * * *